(12) United States Patent
Chang et al.

(10) Patent No.: US 9,357,921 B2
(45) Date of Patent: Jun. 7, 2016

(54) WEARABLE HEALTH MONITORING SYSTEM

(75) Inventors: Hisao M. Chang, Cedar Park, TX (US);
Lusheng Ji, Randolph, NJ (US);
Bernard S. Renger, New Providence, NJ (US)

(73) Assignee: AT&T INTELLECTUAL PROPERTY I, LP, Atlanta, GA (US)

( * ) Notice: Subject to any disclaimer, the term of this patent is extended or adjusted under 35 U.S.C. 154(b) by 1571 days.

(21) Appl. No.: 12/580,950

(22) Filed: Oct. 16, 2009

(65) Prior Publication Data
US 2011/0092779 A1    Apr. 21, 2011

(51) Int. Cl.
| | | |
|---|---|---|
| *A61B 5/00* | (2006.01) | |
| *A63B 71/06* | (2006.01) | |
| *H04W 4/02* | (2009.01) | |
| *A63B 24/00* | (2006.01) | |

(52) U.S. Cl.
CPC ............... *A61B 5/00* (2013.01); *A61B 5/4803* (2013.01); *A61B 5/0022* (2013.01); *A61B 2505/07* (2013.01); *A63B 24/0062* (2013.01); *A63B 71/06* (2013.01); *A63B 71/0619* (2013.01); *H04W 4/02* (2013.01); *H04W 4/023* (2013.01)

(58) Field of Classification Search
CPC ............. H04W 4/02; H04W 4/023–4/028; H04W 64/00; H04W 48/04; A61B 2505/07; A63B 24/0062; A63B 71/06; A63B 71/0619–71/0622
See application file for complete search history.

(56) References Cited

U.S. PATENT DOCUMENTS

| | | | | |
|---|---|---|---|---|
| 5,601,435 | A * | 2/1997 | Quy | 434/307 R |
| 5,748,441 | A * | 5/1998 | Loritz et al. | 361/679.27 |
| 5,883,598 | A * | 3/1999 | Parl et al. | 342/457 |
| 6,113,539 | A * | 9/2000 | Ridenour | 600/300 |
| 6,231,519 | B1 * | 5/2001 | Blants et al. | 600/529 |
| 6,428,449 | B1 * | 8/2002 | Apseloff | 482/3 |
| 6,997,852 | B2 * | 2/2006 | Watterson et al. | 482/1 |
| 7,039,199 | B2 * | 5/2006 | Rui | 381/92 |
| 7,292,151 | B2 * | 11/2007 | Ferguson et al. | 340/573.1 |
| 7,455,622 | B2 * | 11/2008 | Watterson et al. | 482/8 |
| 7,499,711 | B2 * | 3/2009 | Hoctor et al. | 455/456.1 |
| 7,598,878 | B2 * | 10/2009 | Goldreich | 340/573.1 |
| 7,777,622 | B2 * | 8/2010 | Baldus et al. | 340/539.12 |
| 7,822,625 | B2 * | 10/2010 | Brown | 705/2 |
| 7,837,595 | B2 * | 11/2010 | Rice | 482/4 |
| 8,082,030 | B2 * | 12/2011 | Kiviniemi et al. | 600/520 |
| 8,384,516 | B2 * | 2/2013 | Fein et al. | 340/5.84 |
| 2001/0031071 | A1 * | 10/2001 | Nichols et al. | 382/115 |
| 2002/0107433 | A1 * | 8/2002 | Mault | 600/300 |
| 2003/0126593 | A1 * | 7/2003 | Mault | 725/10 |

(Continued)

*Primary Examiner* — William Thomson
*Assistant Examiner* — Shirley Jian
(74) *Attorney, Agent, or Firm* — Guntin & Gust, PLC; Joseph Hrutka (57) ABSTRACT

Devices, systems and methods are disclosed which relate to remotely monitoring the health of an individual. The individual wears a health monitoring device, with an attached strap, capable of sensing characteristics of the individual. These characteristics may include voice level and tone, movements, blood pressure, temperature, etc. The device allows individuals to constantly monitor their health without having to physically visit a doctor or other health care professional. Wireless communication, for instance with an Internet Protocol Television (IPTV) set-top box, allows measurements to be made and evaluated by a 'computerized' healthcare service provider. For a more accurate evaluation, measurements are sent over the INTERNET to a service. The device communicates with services in order to diagnose the individual based upon the characteristics.

20 Claims, 6 Drawing Sheets

(56) References Cited

U.S. PATENT DOCUMENTS

| | | | |
|---|---|---|---|
| 2003/0212311 A1* | 11/2003 | Nova et al. | 600/300 |
| 2004/0037436 A1* | 2/2004 | Rui | 381/92 |
| 2006/0294564 A1* | 12/2006 | Guillorit | 725/108 |
| 2007/0249288 A1* | 10/2007 | Moallemi et al. | 455/68 |
| 2007/0259690 A1* | 11/2007 | Julian et al. | 455/557 |
| 2007/0287928 A1* | 12/2007 | Kiviniemi et al. | 600/508 |
| 2008/0058597 A1* | 3/2008 | Arneson et al. | 600/117 |
| 2008/0061949 A1* | 3/2008 | Ferguson et al. | 340/407.1 |
| 2008/0091087 A1* | 4/2008 | Neuhauser et al. | 600/301 |
| 2008/0091762 A1* | 4/2008 | Neuhauser et al. | 709/201 |
| 2009/0098981 A1* | 4/2009 | Del Giorno | 482/9 |
| 2009/0149257 A1* | 6/2009 | Ferguson et al. | 463/37 |
| 2011/0060235 A1* | 3/2011 | Crompvoets et al. | 600/509 |
| 2013/0018240 A1* | 1/2013 | McCoy | 600/323 |
| 2014/0250447 A1* | 9/2014 | Schink | 725/10 |
| 2014/0371774 A1* | 12/2014 | Hwang et al. | 606/169 |

* cited by examiner

WEARABLE HEALTH MONITORING SYSTEM

BACKGROUND OF THE INVENTION

1. Field of the Invention

The present invention relates to monitoring devices. More specifically, the present invention relates to a wearable health monitoring device for remotely diagnosing patients.

2. Background of the Invention

Visiting a doctor is often important to ensure the health of an individual, not only when the individual is sick, but also for regular check-ups. However, doctor visits can be costly, time consuming, and sometimes unpleasant. Many illnesses require constant visits to the doctor for monitoring. This monitoring may simply be monitoring an individual's blood pressure, determining if any changes have occurred, etc. Unfortunately, to receive this monitoring, the individual may have to drive a long distance, sit in a waiting room, see the doctor, and then drive the long distance home. This is not ideal, as it may end up taking most of, if not all of, the day.

Today there are many health statistics that are important to diagnosing the average individual. Besides statistics like pulse and temperature, muscular flexibility, hand-eye coordination, and basic reflexes are not only useful in everyday circumstances, but are indications of general health. However, since the enactment of The Health Insurance Portability and Accountability Act (HIPAA), certain precautions must be taken to keep this information between the patient and his or her doctor.

When visiting the doctor, people often complain about past conditions or episodes. However, a doctor can only test the patient's current status and ask them questions to recall how they felt during the past episode. Patient accounts can be uninformative and unreliable. Patients largely do not recall things such as instant pulse, blood pressure, temperature, etc. For instance, a patient may remember feeling cold, which can indicate a high temperature, but there is no way for the doctor to determine the exact temperature or even if the patient had a fever at all.

Many individuals would much rather stay in the privacy of their own home. However, the cost of frequent house calls by a doctor or other health care professional is too much for most individuals. Thus, staying at home is currently not a real option.

IPTV is a system through which digital television service is delivered using the architecture and networking methods of Internet protocols over a packet-switched network infrastructure, such as the Internet and broadband Internet access networks, instead of being delivered through traditional radio frequency broadcast and cable television formats.

What is needed is a way to monitor an individual's health while the individual is at home or away from the doctor's office.

SUMMARY OF THE INVENTION

The present invention provides devices and methods for remotely monitoring the health of an individual. The individual wears a health monitoring device, with an attached strap, capable of sensing characteristics of the individual. These characteristics may include voice level and tone, movements, blood pressure, temperature, etc. The device allows the individual to constantly monitor his or her health without having to physically visit a doctor or other health care professional. Wireless communication, for instance with an Internet Protocol Television (IPTV) set-top box allows measurements to be made and evaluated by a 'computerized' healthcare service provider. For a more accurate evaluation, measurements are sent over the INTERNET to a service. The device communicates with services in order to diagnose the individual based upon the characteristics.

Embodiments of the present invention work with an IPTV-based application where an individual uses a health monitoring device, in the form of a wearable wireless voice remote, to interact with a 'computerized' healthcare service provider at his or her home. The individual interacts with the service using their voice and body movements, such as touching the nose or the toe within a defined time window, according to the video instructions showing on the IPTV screen. The invention collects data based upon these interactions as well as inputs of the individual's health statistics, such as pulse, temperature, etc. in order for a live or virtual health care professional to diagnose the individual.

In an exemplary embodiment of the present invention, the invention is a device for monitoring health. The device includes a processor, a memory in communication with the processor, a remote health monitor logic on the memory, a health profile database on the memory, a wireless transceiver in communication with the processor, a housing enclosing the processor, the memory, and the wireless transceiver, a microphone in communication with the processor, a speaker in communication with the processor, and a strap coupled with the housing. A set-top box receives a voice sample and detects a distance of the wireless transceiver from the set-top box to monitor a user's health by producing an audio tone from a speaker; sending a data packet from the set-top box at the same time the audio tone is produced; and calculating the distance using the difference in time between receipt of the audio tone by the microphone and the data packet by the wireless transceiver.

In another exemplary embodiment of the present invention, the invention is a system for monitoring health. The system includes a wireless health monitoring device, a set-top box having a box memory in communication with the wireless health monitoring remote, and a box health monitor logic on the box memory. The set-top box receives a voice sample and detects a distance of the wireless transceiver from the set-top box to monitor a user's health by producing an audio tone from a speaker; sending a data packet from the set-top box at the same time the audio tone is produced; and calculating the distance using the difference in time between receipt of the audio tone by the microphone and the data packet by the wireless transceiver.

In a further exemplary embodiment of the present invention, the invention is a method for monitoring health. The method includes connecting a health monitoring device to a set-top box, receiving a health sample from the health monitoring device, receiving a voice sample from the health monitoring device, evaluating the voice sample with a voice baseline, instructing a user to perform a physical move, receiving a position sample determinative of the physical move, and evaluating the position with a position baseline using time difference of arrival between an audio tone and a data packet.

DETAILED DESCRIPTION OF THE INVENTION

The present invention provides devices and methods for remotely monitoring the health of an individual. The individual wears a health monitoring device, with an attached strap, capable of sensing characteristics of the individual. These characteristics may include voice level and tone, movements, blood pressure, temperature, etc. The device allows the individual to constantly monitor his or her health without having to physically visit a doctor or other health care professional. Wireless communication, for instance with an Internet Protocol Television (IPTV) set-top box allows measurements to be made and evaluated by a 'computerized' healthcare service provider. For a more accurate evaluation, measurements are sent over the INTERNET to a service. The device communicates with services in order to diagnose the individual based upon the characteristics.

Embodiments of the present invention work with an IPTV-based application where an individual uses a health monitoring device, in the form of a wearable wireless voice remote, to interact with a 'computerized' healthcare service provider at his or her home. The individual interacts with the service using his or her voice and body movements, such as touching the nose or the toe within a defined time window, according to the video instructions showing on the IPTV screen. The invention collects data based upon these interactions as well as inputs of the individual's health statistics, such as pulse, temperature, etc. in order for a live or virtual health care professional to diagnose the individual.

In IPTV-based embodiments, an IPTV-based video-oriented service is presented to the patient either through a pre-recorded video of a human medical service provider, such as an orthopedic surgeon, or an interactive video session with a computer-animation based avatar. In embodiments using an avatar, the patient follows the instructions provided by the 'virtual doctor' on the IPTV screen to report and/or show his or her health status through speech, body movement, walking, stretching, etc.

With a health monitoring device and a pre-paid (or pay-per-visit) healthcare plan offered by the IPTV-based service provider, the patient completes a routine check-up at his or her home by interacting with a virtual doctor over IPTV. The patient responds to the video instructions shown on the IPTV screen through physical responses in real time such as using his or her voice (vocal level, intelligibility, clarity, recall/repeat the words heard from the videos and/or from memory) and body movements (attempt a physical reach in responding to an instruction like 'please press and hold Talk button and touch your left toe'). The system records the patient's spatial-temporal movement via distance and direction measurements between the health monitoring device and a reference position such as the TV or the transceiver connected to the IPTV set-top box, the speed with which the patient moves, visual/cognitive alertness through answering the questions imposed by the virtual doctor on the IPTV screen, motor skills, etc. For example, the virtual doctor may ask the patient to report the objects displayed on the TV via voice response in a given time window in order to determine alertness. Motor skill may be determined by following the instructions given by the virtual doctor on the IPTV screen, such as "please press Talk button three times while you walk towards me (i.e., towards the TV)" or "please say 'I am ok' after you slowly bend your body forward towards the floor and repeat this 5 times".

For example, the user may complain of an injured shoulder. The doctor or virtual doctor, through the IPTV set-top box, may tell the user to raise his or her hand in order to test the user's range of motion. The user holds the health monitoring device in his or her hand and moves the arm as instructed. The distance and direction from the health monitoring device are detected by the IPTV set-top box. These distance and directional readings are processed by the processor according to a box health monitor logic employing algorithms of the IPTV set-top box, herein explained below, to determine the movements that were made by the user. These readings may be used alone or compared with baseline readings for the user in order to determine whether the user has a limited range of motion. If so, the limited range of motion becomes a factor in the diagnosis of the user.

In an exemplary embodiment when the TV and the set-top box are placed close together, or a designated speaker is placed close to the set-top box, the distance between the health monitoring device and, for instance, the TV, can be determined by measuring the time difference of arrival (TDOA) between two signals, both of which are issued by the set-top box. For TV embodiments, a user may select to use an internal speaker or an external speaker in communication with the TV as the designated speaker. For speaker embodiments, the designated speaker can be a small dedicated speaker coupled to or within the set-top box, or one in a set of external speakers such as in a surround sound system. In either embodiment, the user selects the speaker closest to the set-top box to use as the designated speaker. The first signal is a data packet sent by the IPTV set-top box to the health monitoring device over their wireless data communication channel. The second signal is a specific audio tone played by the designated speaker as commanded by the IPTV set-top box. The timing of issuance of the set-top box commands which result in the two signals should compensate for various delays such as the command processing delay and designated speaker response delay so that both signals begin simultaneously. Because the data packet is transmitted over RF, the health monitoring device shall receive the packet prior to detecting the audio tone. The difference in time between receiving the packet and detecting the tone is used to calculate the distance between the designated speaker and the health monitoring device. Denoting the distance to be calculated as D, the propagation speed of audio tone as $V_a$ and the propagation speed of radio as $V_r$, the measured time difference as T, their relationship can be expressed as:

$$D/V_a - D/V_r = T$$

or further:

$$D = TV_a V_r/(V_r - V_a).$$

Alternately, a designated speaker may not be near the set-top box. Geometry can be used to correct for the difference in distance between the set-top box and the health monitoring device, and the designated speaker and the health monitoring device. When there are multiple audio speakers in the TV room, a designated speaker may not be selected. The TDOA method described above is used to find the distances between the health monitoring device and each of the speakers. Combining these distances with the known distances among the speakers themselves, the direction from the TV to the health monitoring device can be computed with simple geometry.

When the set-top box and the TV are not co-located, the time difference between the two signals can be used in motion/movement related diagnostics. For instance, the time difference between the two signals can be used to measure a change in relative position. Baseline TDOA measurements can be taken while the patient is in a normal condition and future diagnostic TDOA measurements can be compared with this baseline profile.

Various modes of using the present invention are also possible. In a network mode, the health monitoring device and/or the IPTV set-top box is connected to a network in communication with a live or virtual health care professional. In a local mode, the health monitoring device communicates with the IPTV set-top box to record various measurements either for a diagnosis based upon a database on the IPTV set-top box or for later sending to a network. A non-connected mode allows a user to carry the health monitoring device with them to record measurements throughout the day. These measurements are stored on a memory of the health monitoring device and are later sent to the IPTV set-top box or network when these are in communication with the health monitoring device.

Embodiments of the invention allow users to input various demographic categories they belong to as well as other symptoms they are having. These inputs provide the live or virtual healthcare professional information that may be important in diagnosing the user. For instance, the user may enter his or her age, height, and weight as well as flu-like symptoms he or she is having.

For the following description, it can be assumed that most correspondingly labeled structures across the figures (e.g., 132 and 232, etc.) possess the same characteristics and are subject to the same structure and function. If there is a difference between correspondingly labeled elements that is not pointed out, and this difference results in a non-corresponding structure or function of an element for a particular embodiment, then that conflicting description given for that particular embodiment shall govern.

Figure 1:
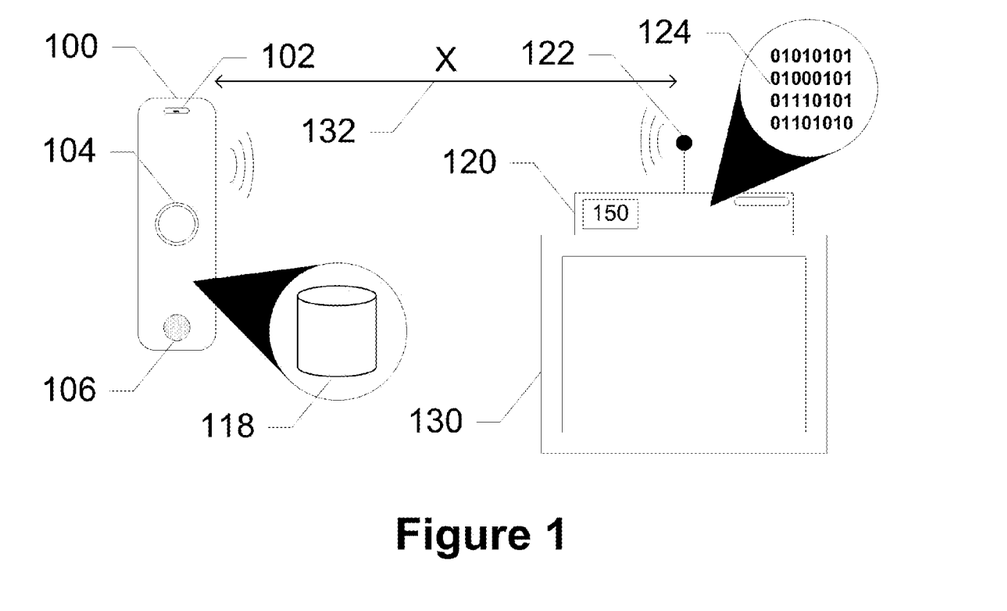
FIG. 1 shows a system for monitoring health, according to an exemplary embodiment of the present invention.

FIG. 1 shows a system for monitoring health, according to an exemplary embodiment of the present invention. This system may be used at the local level, or may be connected to a network. In this embodiment, the system includes a health monitoring device 100, a set-top box 120, and a television 130. Health monitoring device 100 includes a push button 104, a microphone 102, a speaker 106, and a health profile database 118 on a memory. Health monitoring device 100 is a small wireless device capable of detecting the user's voice, movements, health statistics, etc. Health monitoring device 100 attaches to a user, such as with an attached strap. Health monitoring device 100 may take an ergonomic form such that it fits comfortably in the user's hand. Health monitoring device 100 uses various sensors to take readings on the user as well as the user's environment. These reading may include the user's temperature, the room temperature, the user's pulse, the oxygen level in the user's blood, the user's blood sugar level, the user's blood alcohol level, the user's pupil dilation, the user's pupil movement, the user's range of motion, the user's speed of motion, as well as other readings generally taken at a doctor's office. The sensors used may be integrated into health monitoring device 100 or may be coupled to health monitoring device 100 using adaptors. A wireless transceiver within health monitoring device 100 communicates with a transceiver 122 on set-top box 120 to detect motion of the user, receive commands from set-top box 120, send data to set-top box 120, etc. A distance 132 between the wireless transceiver and transceiver 122 is determined. The wireless transceiver in health monitoring device 100 may use Radio Frequency (RF) communication technologies such as cellular, wireless personal area networks, e.g., BLUETOOTH wireless networks, wireless local area networks, e.g., WI-FI wireless networks, low-rate wireless personal area networks, e.g., ZIGBEE wireless networks, radiofrequency identification (RFID), Ultra Wide Band (UWB), etc., or optical communication technologies such as infrared (IR), laser, Visible Light Communication (VLC), etc. Push button 104 on health monitoring device 100 allows the user to respond to commands from or initiate commands to set-top box 120 or health monitoring device 100. Push button 104 may be used to signify the start of movements, can turn microphone 102 on or off, etc. In other embodiments, push button 104 is a touch-sensitive biometric multifunction sensor. Push button 104 may also serve to authenticate the user, as in some embodiments push button 104 includes a fingerprint scanner or other biometric reader or optical scanner. Other authentication methods may be through voice authentication when the user presses push button 104, iris authentication, etc. Authentication is useful for health monitoring device 100, as the monitoring of the user may be compared with previous sessions, the diagnosis of the individual may be private, etc., and the identity of the individual is important. Additionally, push button 104 may detect the user's pulse, dexterity, etc. Speaker 106 gives the user commands, alerts the user, etc. For instance, in a non-connected mode, the user may not be near IPTV set-top box 120 or television 130 and must otherwise receive commands. Microphone 102 provides an input for speech or sounds from the user. This may be in response to commands from television 130 or set-top box 120, to select functions, to call for help, etc. Health profile database 118 stores inputs, vital signs, etc. from the user. Health profile database 118 also contains baseline values for users of the device. These baseline values may be set by the user at an initial diagnosis, when setting up the system, etc. or may be set at the office of a doctor or healthcare professional.

Set-top box 120 includes a remote health monitoring logic 124 on a memory and a transceiver 122. Remote health monitoring logic 124 includes instructions for set-top box 120 to interact with health monitoring device 100. These instructions are carried out by a processor on set-top box 120 which commands other components of set-top box 120. Transceiver 122 may be a USB-based wireless local area network, e.g., a USB-based WI-FI wireless network, Access Point in communication with IPTV set-top box 120, an integrated transceiver, etc. Transceiver 122 allows set-top box 120 to connect with a network. This allows set-top box 120 to communicate with application servers, allowing the user to communicate with real and/or virtual 12 doctors, etc. Transceiver 122 also communicates with the wireless transceiver of health monitoring device 100 to receive inputs from health monitoring device 100, send outputs to health monitoring device 100, etc. Set-top box 120 communicates with television 130 using a wireless or wired connection. Television 130 displays visual output from set-top box 120. This may be instructions for the user, the user's results, diagnoses, etc.

In embodiments of the present invention, a protocol for setting baseline values enables the user to set baseline values at the doctor's office without the health monitoring device being at the office. This may be accomplished by using a similar health monitoring device to record baseline values or by using a plurality of other devices, such as a blood pressure cuff, a thermometer, etc., to set these values. These baseline values may be remotely set, with the office or service provider allowing the user to download the values or sync the values with the health monitoring device. In this way, all the patient records are at the doctor's office, but certain values like these baseline values may be sent to the device.

In embodiments of the present invention, the health monitoring device may take the form of earrings or may be embedded under the skin of the user. With earrings, the position and orientation of the user's head may easily be determined using wireless signals between wireless transceivers in the earrings and a transceiver on the IPTV set-top box. When embedded under the skin, the orientation and location of the embedded device is determined. By embedding the health monitoring device under the skin, other health statistics may also be taken.

In further embodiments of the present invention, the remote health monitoring logic may be stored on the memory of the health monitoring device and/or on a network in communication with the IPTV set-top box. By having the remote health monitoring logic in multiple locations, the different modes of the invention can be fully used.

Embodiments of the present invention use one or more adaptors to attach various measurement devices. The health monitoring device may include a finger clip for measuring the blood pressure of the user or may include an adaptor to attach such a finger clip. Similarly, the health monitoring device may include an adaptor for a stethoscope or other device.

Figure 2:
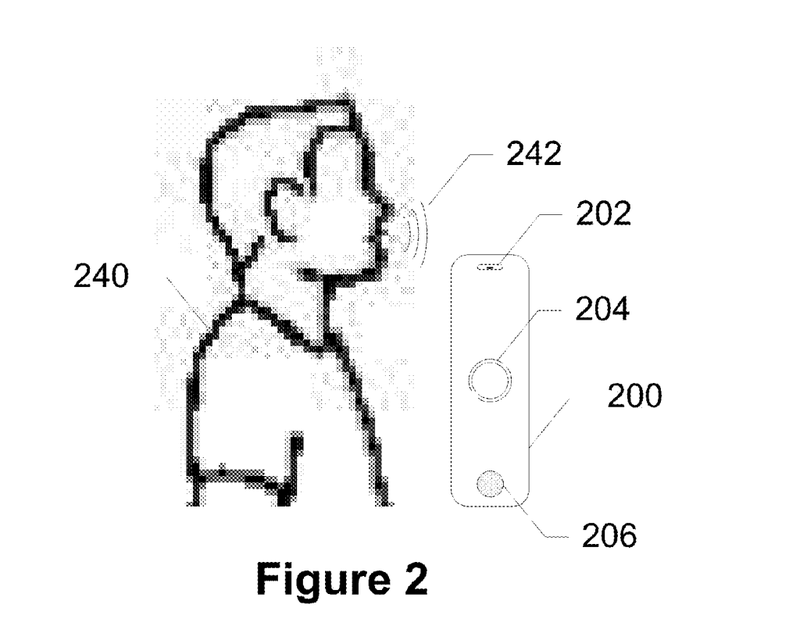
FIG. 2 shows a user interacting with a health monitoring device, according to an exemplary embodiment of the present invention.

FIG. 2 shows a user 240 interacting with a health monitoring device 200, according to an exemplary embodiment of the present invention. In this embodiment, health monitoring device 200 is used to measure user 240's speech. Users complaining of sore throats, coughing, and/or other illnesses or diseases often have discernable differences in their speech. Determining these differences may assist in the diagnosis of these users. In order to determine whether user 240's voice is different, user 240 first must record a baseline recording. This may be done during the initial setup of the system and health monitoring device 200, during the onset of symptoms, at an initial checkup, etc. and may be done by user 240 at home, with the assistance of a doctor at the doctor's office, etc. In order to create a baseline recording, user 240 speaks into microphone 202 of health monitoring device 200. Health monitoring device 200, an IPTV set-top box connected to a television, or a medical professional may instruct user 240 to say a word, phrase, etc. into microphone 202. When health monitoring device 200 instructs user 240, instructions are delivered through speaker 206. Health monitoring device 200 records user 240's speech 242 to a memory on health monitoring device 200, a memory on the IPTV set-top box, a memory on a network, etc. If the recorded speech has not been made or used before, the recorded speech is set as a baseline recording. If a baseline recording has already been created, the recorded speech is compared with the baseline recording. Differences in patterns, volume, tone, inflection, etc. are determined to assist with the diagnosis of the patient. The comparison may be done by a processor on health monitoring device 200, by a processor on the IPTV set-top box, by a processor on the network, etc.

Figures 3A, 3B:
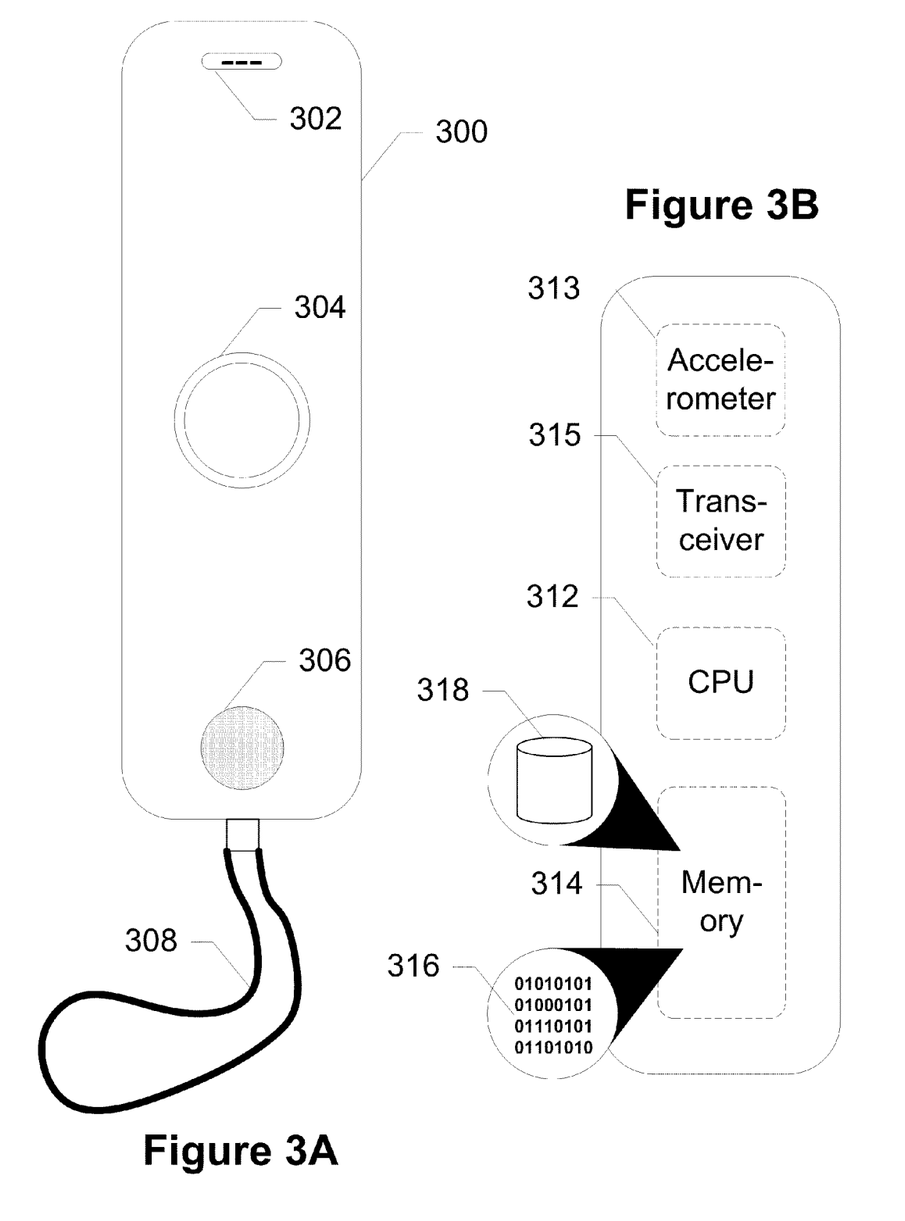
FIGS. 3A and 3B show a health monitoring device and its components, according to an exemplary embodiment of the present invention.

FIGS. 3A and 3B show a health monitoring device 300 and its components, according to an exemplary embodiment of the present invention. Health monitoring device 300 may be used alone in a non-connected mode, may be used in conjunction with an IPTV set-top box in a local mode, or may be used in a network mode with a live or virtual healthcare professional. In this embodiment, health monitoring device 300 includes a microphone 302, a speaker 306, a push button 304, a strap 308, a wireless transceiver 315, a central processing unit 312, and a memory 314. Strap 308 wraps around the neck of the user. Strap 308 is a stretchable material, such as a coiled plastic ring resembling a common telephone cord. Strap 308 may be stretched in order for the user to move with health monitoring device 300 and may retract such that it is near the user's mouth when the user is speaking into microphone 302. Speaker 306 allows the user to receive instructions, listen to diagnoses, listen to music or a game, etc. Push button 304 provides an input and/or a switching mechanism as well as an input for authentication. Push button 304 may be used in order to switch microphone 302 on and off. Additionally, push button 304 may contain sensors in order to monitor the user's pulse, the user's temperature, the room temperature, etc. Microphone 302 provides an input for health monitoring device. Microphone 302 detects voice volume, tone, inflection, etc. and sends this data to CPU 312. These may be compared with baseline values previously stored in health monitoring device 300 or by an IPTV set-top box or server on a network. When comparing with baseline values on health monitoring device 300, CPU 312 runs a remote health monitor logic 316 on memory 314 that compares the values recorded by microphone 302 with values stored on a health profile database 318 on memory 314. CPU 312 commands components of health monitoring device 300 according to remote health monitor logic 316 as well as other logic on memory 314. Memory 314 stores logic, data, etc. Together, CPU 312 and memory 314 may serve to buffer speech and or movement data to ensure the data is accurate. Memory 314 also stores device identification in order to authenticate health monitoring device 300 with an IPTV set-top box and/or network. Health profile database 318 stores data concerning the user or users. This data may include a personal profile including height, weight, body fat, medical history, etc. as well as data received from user inputs. These user inputs may be in response to instructions from a doctor, a virtual doctor, etc. Wireless transceiver 315 allows health monitoring device 300 to wirelessly communicate with a network, other wireless devices such as an IPTV set-top box, etc. Wireless transceiver 315 may use Radio Frequency (RF) communication technologies such as cellular, wireless personal area networks, e.g., BLUETOOTH wireless networks, wireless local area networks, e.g., WI-FI wireless networks, low-rate wireless personal area networks, e.g., ZIGBEE wireless networks, radio-frequency identification (RFID), Ultra Wide Band (UWB), etc., or optical communication technologies such as infrared (IR), laser, Visible Light Communication (VLC), etc.

Embodiments of the present invention also include an accelerometer 313 within health monitoring device 300. Accelerometer 313 determines the orientation of health monitoring device 300. Accelerometer 313 is also used to detect motions of health monitoring device 300, such as for performing requested motions, playing games, etc. In embodiments of the present invention, accelerometer 313 is sensitive such that it may also be used to determine the pulse of the user, as the pulse creates small movements. Readings from accelerometer 313 are sent to CPU 312 to assist health monitoring device 300 in determining the extent of motions by the user.

Figures 4A, 4B, 4C:
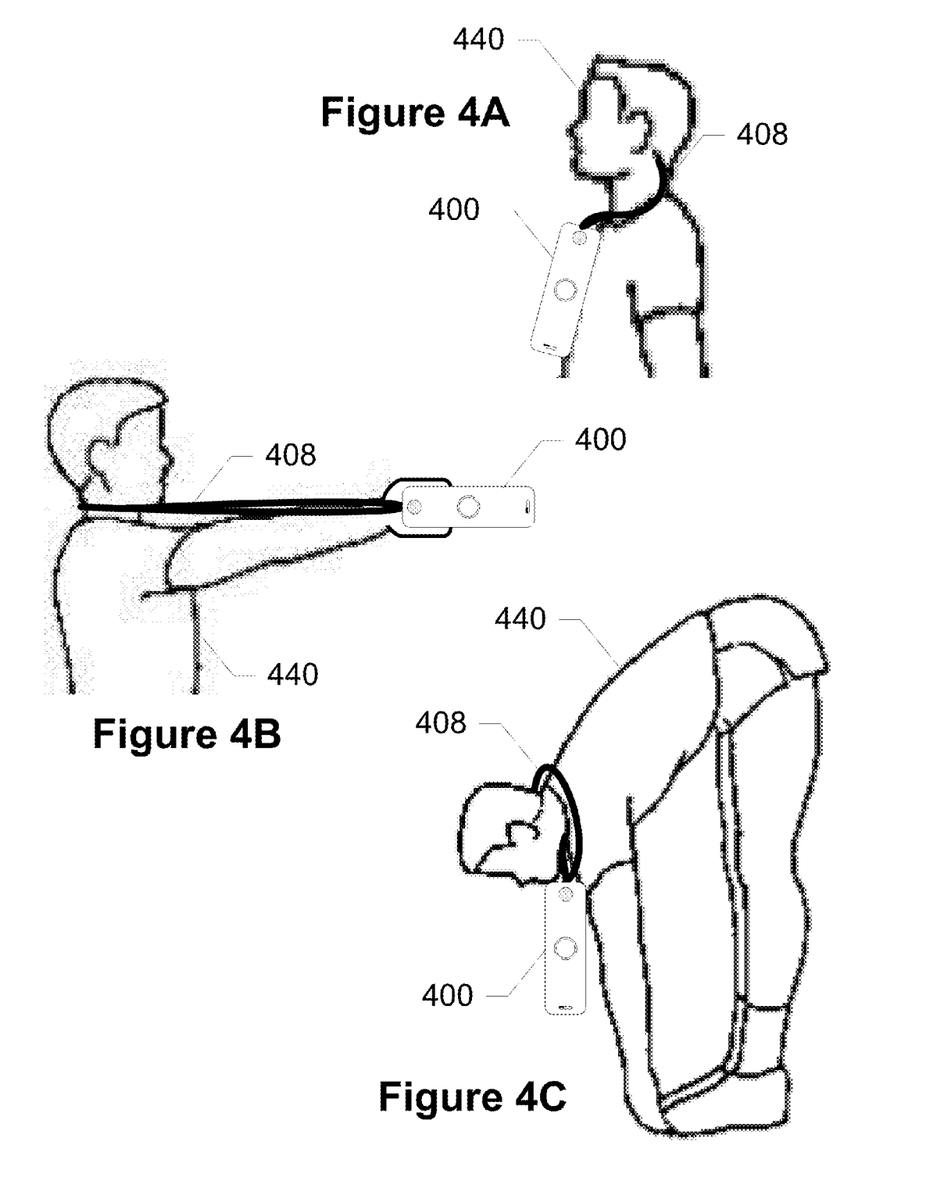
FIGS. 4A, 4B, and 4C show a user performing tasks with a health monitoring device according to instructions, according to an exemplary embodiment of the present invention.

FIGS. 4A, 4B, and 4C show a user 440 performing tasks with a health monitoring device 400 according to instructions, according to an exemplary embodiment of the present invention. These instructions may be delivered by health monitoring device 400, by an IPTV set-top box connected to a television, by a live or virtual medical professional, etc. In each of these embodiments, user 440 is wearing a strap 408 around user 440's neck. Strap 408 is a stretchable material such that user 440 can hold health monitoring device 400 in his or her hand and perform motions. When health monitoring device 400 is not in user 440's hand, health monitoring device 400 is closer to user 440's mouth and ears such that user 440 can receive instructions, make voice commands, record speech, etc.

FIG. 4A shows a user 440 recording speech on a health monitoring device 400, according to an exemplary embodiment of the present invention. In this embodiment, a strap 408 is around user 440's neck. Health monitoring device 400 is in a position to instruct user 440 and record user 440's speech. Health monitoring device 400 is hanging, with strap 408, in an unstretched position. This position is recorded by the health monitor logic and serves as a base position from which the movement in the next Figures is measured.

FIG. 4B shows a user 440 performing arm motions with a health monitoring device 400, according to an exemplary embodiment of the present invention. In this embodiment, a strap 408 is around user 440's neck and user 440 is extending an arm out in response to a command from health monitoring device 400 or an IPTV set-top box through a television. This embodiment is useful, for instance, when measuring user 440's range of motion. The distance moved by health monitoring device 400, the speed of movement, angles of movement, etc. are recorded by health monitoring device as data. This data may be compared with baseline data from the position in FIG. 4A to determine if user 440's movement is limited. When a baseline is taken right after an injury, it can be determined from the data whether user 440's injury is improving. When a baseline is taken when user 440 is healthy, the data can determine limitations in user 440's motion. The data is determined by measurements made by components of health monitoring device 400 and/or the IPTV set-top box. These measurements may use changes in distance and direction from the health monitoring device to a reference position such as the TV using accelerometer measurements, etc. in order to determine user 440's movement. Measurements are sent through a processor of health monitoring device 400 and/or the IPTV set-top box to determine the movements and compare the movements with the baseline data.

FIG. 4C shows a user 440 wearing a health monitoring device 400 and bending over at the waist, according to an exemplary embodiment of the present invention. In this embodiment, user 440 has a strap 408 connected to health monitoring device 400 around user 440's neck. User 440 has been instructed to touch his or her toes. With strap 408 around user 440's neck, user 440 slowly bends at the waist to touch the toes. The location of health monitoring device 400 moves as user 440 bends lower. Measurements of the distance bent down as well as other measurements are taken by health monitoring device 400 using infrared, wireless local area networks, e.g., WI-FI wireless networks, TDOA, accelerometers, etc. similar to the measurements in FIG. 4B. These measurements may be compared to a baseline measurement, may form the baseline measurement, etc.

Figure 5:
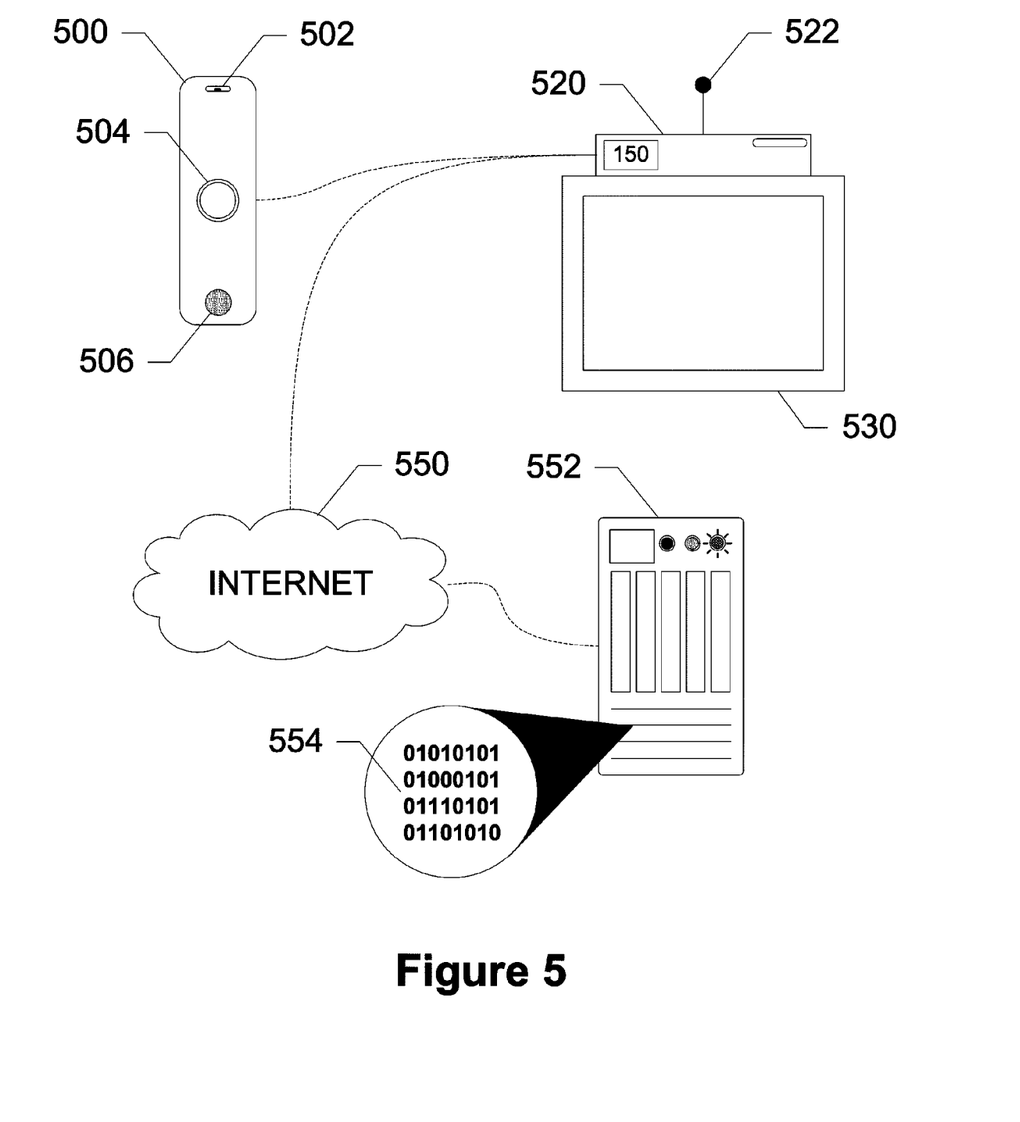
FIG. 5 shows a network-based system for monitoring health, according to an exemplary embodiment of the present invention.

FIG. 5 shows a network-based system for monitoring health, according to an exemplary embodiment of the present invention. In this embodiment, a health monitoring device 500 and/or an IPTV set-top box 520 are in communication with a server 552 connected through Internet 550. This allows the user to communicate and send data back and forth with a live or virtual health care professional. When taking voice measurements, voice measurements recorded by a microphone 502 of health monitoring device 500 are sent through a wireless transceiver of health monitoring device 500 to a transceiver 522 of IPTV set-top box 520. Transceiver 522 forwards these voice measurements over Internet 550 to server 552 where they may be processed by a processor based upon a remote health monitor logic 554 on a memory of server 552. Measurements taken by push button 504 may be similarly forwarded to server 552. Server 552 may be an IPTV healthcare service node with automatic speech recognition (ASR) with speaker adaptation capability. This allows server 552 to recognize speech from the user. When sending commands to the user, server 552 sends commands over Internet 550 to transceiver 522 of IPTV set-top box 520. These commands may be selected from a database on server 552 or network 550 based upon remote health monitor logic 554. A health care professional may upload these commands as well as diagnoses to the database of server 552. The commands are either delivered through television 530 connected to IPTV set-top box 520 or are forwarded through transceiver 522 to health monitoring device 500 where they are delivered through a speaker 502.

In embodiments of the present invention using a live doctor or other healthcare professional, the doctor can similarly connect to the server using an IPTV set-top box, video conferencing equipment, etc. In this way, the doctor communicates directly with the user over the Internet. In embodiments utilizing a virtual healthcare professional, a memory, a processor, and the remote health monitor logic on the server store and determine responses or diagnoses based upon inputs by the user.

In embodiments of the present invention, the system may use games and/or videos in order to test user responses or to calibrate the health monitoring device. These games and/or videos may be stored on the server, on the IPTV set-top box, etc. Using the health monitoring device for games allows the system to determine, for instance, the ability to follow commands, testing cognitive functioning, etc. Games may also serve to test the user's flexibility, reaction time, range of motion, etc. Games or videos may also be used when calibrating the health monitoring device or setting a baseline. Games may be used to establish certain motions within the system for calibration. Games or videos may be used, for instance, to raise the user's heart rate to a certain level necessary for calibration or a baseline.

Figure 6:
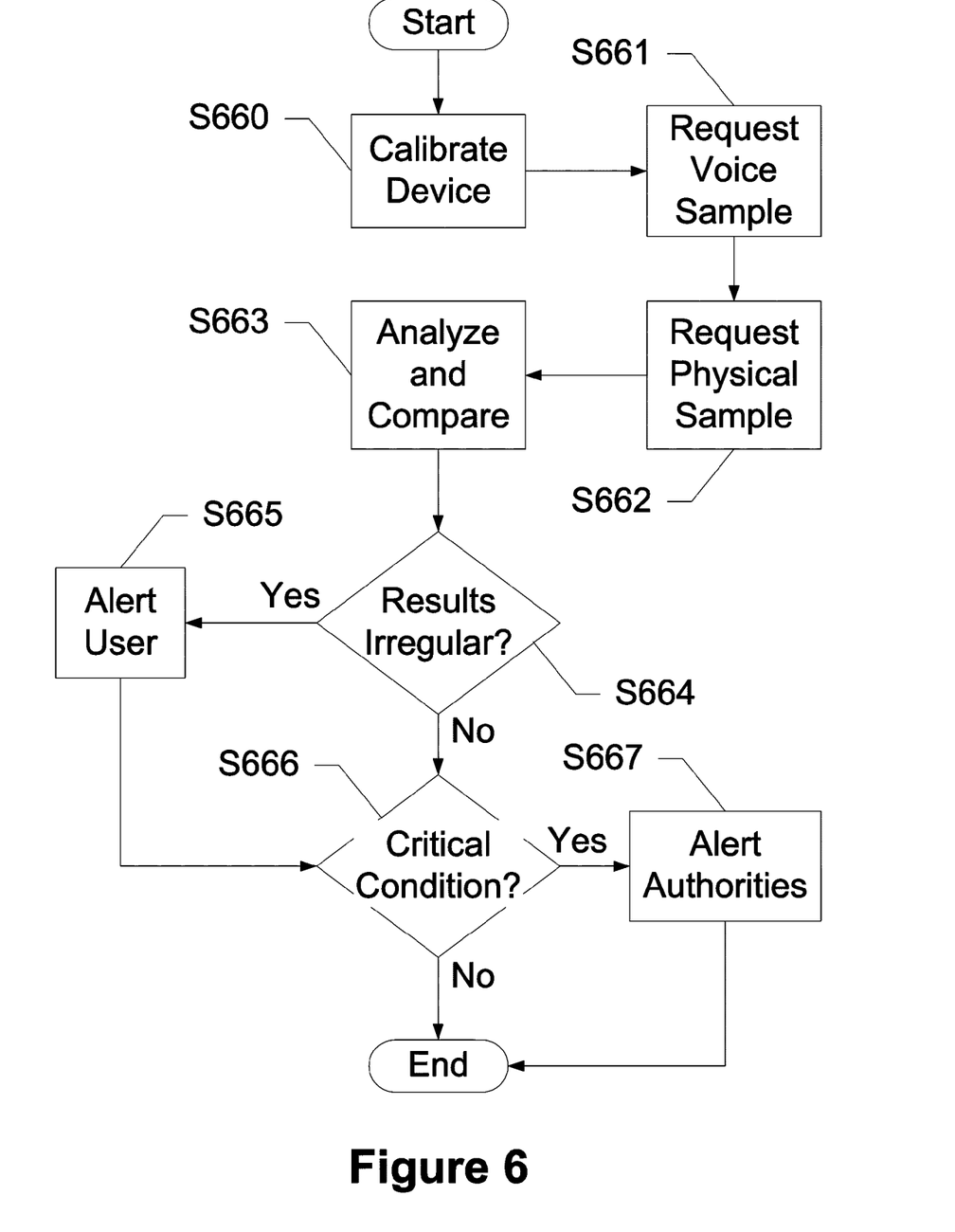
FIG. 6 shows a method of remotely monitoring health, according to an exemplary embodiment of the present invention.

FIG. 6 shows a method of remotely monitoring health, according to an exemplary embodiment of the present invention. In this embodiment, the method begins by calibrating the health monitoring device S660. The calibration may be accomplished by setting baseline levels for speech, motions, positions, etc. With the health monitoring device calibrated, the health monitoring device or an IPTV set-top box through a television requests a voice sample from the user S661. The user speaks into the microphone of the health monitoring device which records the voice sample. The health monitoring device or IPTV set-top box then requests a physical sample S662. For example, the user may be requested to bend at the waist as far as possible. A transceiver on the IPTV set-top box communicates with a wireless transceiver of the health monitoring device to create data for the physical sample. With the voice sample and/or the physical sample, a processor, according to logic on a memory, analyzes the data and compares the voice sample and/or physical sample with baseline samples S663. The analyzing includes compiling the inputs to determine characteristics of the voice sample and/or physical sample. The comparison determines whether the voice sample and/or physical sample are different than the baseline samples and, if so, how they are different. These differences help to influence the diagnosis. The processor determines whether the results are irregular S664. A result is irregular if the voice sample and/or physical sample is different from the baseline sample by a set amount. This may be an amount set by the healthcare professional based upon the test being performed. If the results are irregular, the user is alerted S665. If the results are not irregular but the user is not appropriately responding, the user or the processor may determine that the user is in critical condition S666. This may be if the user is not showing a pulse, not responding to prompts, etc. The user or processor may also determine that the user is in critical condition S666 after the user has been alerted S665. If the user or processor does not signal that the user is in critical condition, the method ends. If the user is in critical condition, the health monitoring device, the IPTV set-top box, or a server on the network alerts authorities S667. The user may be given a certain window of time to respond before notifying authorities. For instance, the system may automatically call an ambulance to the location of the user if the user has been prompted and does not respond within five minutes.

Figure 7:
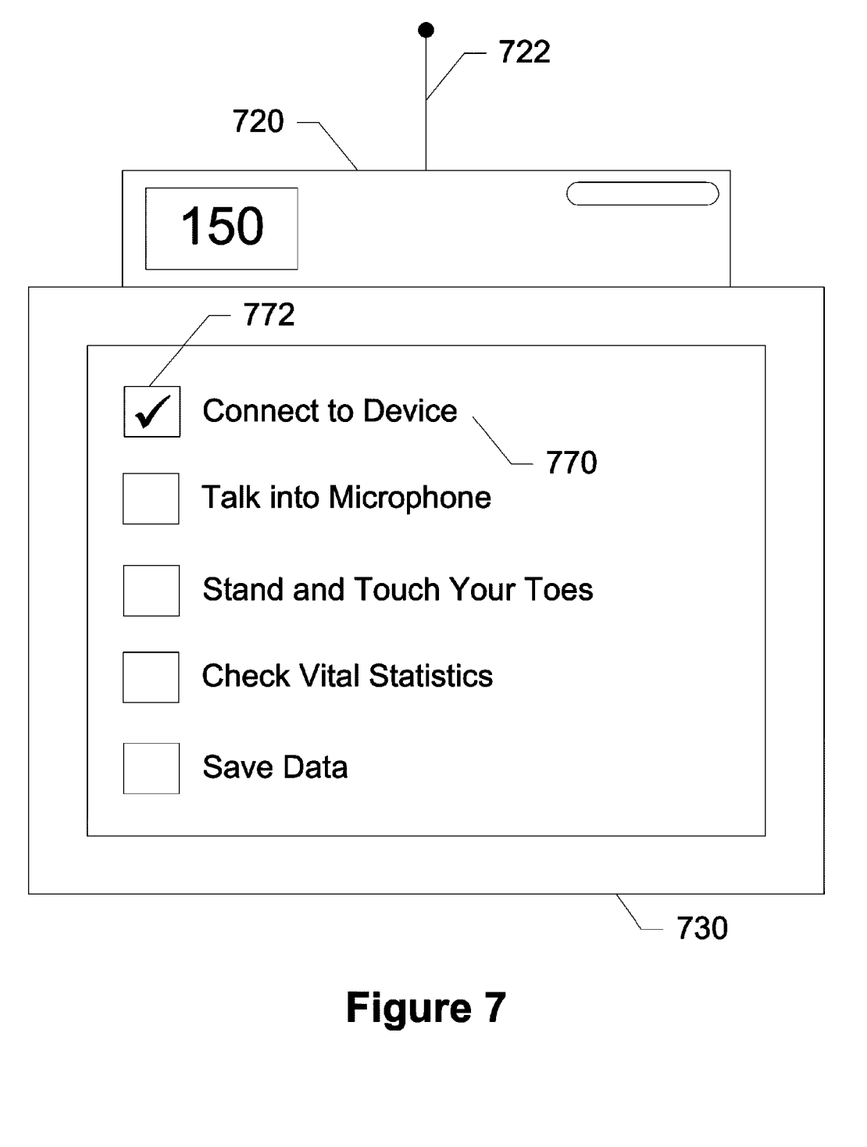
FIG. 7 shows an IPTV set-top box and a television listing instructions, according to an exemplary embodiment of the present invention.

FIG. 7 shows an IPTV set-top box 720 and a television 730 listing instructions, according to an exemplary embodiment of the present invention. In this embodiment, IPTV set-top box 720 communicates with a health monitoring device to determine whether the user is responding to the instructions. The instructions are viewed on the screen of television 730. Each instruction is listed with a corresponding check box that is marked when the instruction is completed by the user with the health monitoring device. For instance, in the figure, the first instruction is to connect the health monitoring device 770. The user has already connected the health monitoring device to the IPTV set-top box. Thus, check box 772 has been marked.

All of the aforementioned combinations should be customizable to suit the user. In some cases it may even be advantageous to provide input models suited to various disabilities, thus improving the usefulness of the device for the largest possible user base. Beyond initial settings, this mechanism should be automatic, autonomous and much more user friendly than the alternatives.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A device, comprising:
a memory that stores executable instructions;
a processor coupled to the memory; and
a wireless transceiver in communication with the processor, wherein the processor, responsive to executing the instructions, facilitates performance of operations comprising:
capturing a first input representing a baseline health performance sample of a user of the device;
receiving a request for a new health performance sample from a set-top box device by way of the wireless transceiver;
capturing a second input representing the new health performance sample according to the request, wherein the first and second inputs comprises measurements corresponding to movement of a health monitoring device relative to the set-top box device, wherein the movement is determined according to a time difference of arrival at the health monitoring device between two signals originating at the set-top box device;
comparing the second input representing the new health performance sample to the first input representing the baseline health performance sample to determine a difference in user health performance;
determining a health condition of the user based on the difference in user health performance; and
transmitting information regarding the health condition to the set-top box device by way of the wireless transceiver for reporting to an internet protocol television network.

2. The device in claim 1, wherein the health condition comprises one of mental function, physical function, pulmonary function, or state of consciousness, and wherein a first signal of the two signals originating at the set-top box device comprises a data packet and a second signal of the two signals originating at the set-top box device comprises an audio tone, wherein a distance between the health monitoring device and the set-top box device is determined according to a time difference of arrival between the first and second signals at the health monitoring device.

3. The device in claim 1, wherein the first input representing the baseline health performance sample comprises a first voice sample of the user and wherein the second input representing the new health performance comprises a second voice sample and further comprising a microphone to capture the first voice sample and the second voice sample.

4. The device in claim 1, wherein the first input representing the baseline performance sample comprises a first movement sample of the user and wherein the second input representing the new performance comprises a second movement sample.

5. The device in claim 4, wherein the health monitoring device comprises an accelerometer adapted for capturing the first movement sample and the second movement sample.

6. The device in claim 1, further comprising:
uploading the baseline health performance sample by way of the internet protocol television network;
receiving another request for a subsequent performance sample of the user from the set-top box device by way of a wireless communication link to the set-top box device;
capturing the subsequent performance sample of the user by way of the health monitoring device;
downloading the baseline health performance sample by way of the internet protocol television network, resulting in a downloaded baseline health performance sample;
comparing the subsequent performance sample to the downloaded baseline performance sample to determine an updated difference of user performance;
determining an updated health condition of the user based on the updated difference in user health performance; and
transmitting information regarding the health condition to the set-top box device by way of the wireless transceiver for reporting to the internet protocol television network.

7. A machine-readable storage medium, comprising executable instructions that, when executed by a processor, facilitate performance of operations, comprising:
 receiving a request for a performance sample of a user from a set-top box by way of a wireless communication link to the set-top box, wherein the performance sample comprises a measurement corresponding to a movement of a sensor, wherein the sensor is in communication with the set-top box, relative to the set-top box, wherein the movement is determined according to a time difference of arrival at the sensor between two signals originating at the set-top box;
 capturing the performance sample of the user by way of the sensor;
 comparing the performance sample to a baseline performance sample to determine a difference of user performance;
 determining a condition of the user based upon the difference in user performance; and
 transmitting the condition of the user to the set-top box by way of the wireless communication link for reporting to an internet protocol television network.

8. The machine-readable storage medium in claim 7, wherein the performance sample comprises a vocal signal.

9. The machine-readable storage medium in claim 8, wherein the sensor comprises a microphone.

10. The machine-readable storage medium in claim 7, wherein the performance sample comprises a movement signal, wherein a first signal of the two signals originating at the set-top box comprises a data packet and a second signal of the two signals originating at the set-top box comprises an audio tone, wherein a distance between the sensor and the set-top box is determined according to a time difference of arrival between the first and second signals at the sensor.

11. The machine-readable storage medium in claim 10, wherein the sensor comprises an accelerometer.

12. The machine-readable storage medium in claim 7, wherein the operations further comprise presenting the request for the performance sample to the user by way of an audio speaker, wherein the audio speaker is associated with the set-top box.

13. The machine-readable storage medium in claim 7, wherein the request for the performance sample originates from a doctor in communication with the set-top box by way of an application server of an internet protocol television network.

14. The machine-readable storage medium in claim 7, wherein the operations further comprise:
 capturing a second performance sample by way of the sensor;
 determining that the wireless communication link to the set-top box is not available; and
 storing the second performance sample in a memory until the wireless communication link is available.

15. A method for monitoring health, the method comprising:
 connecting, by a device comprising a processor, to a set-top box;
 receiving, by the processor, a voice sample of a person via a microphone of the device;
 evaluating, by the processor, the voice sample against a voice baseline to identify the person;
 receiving, by the processor, an instruction from the set-top box;
 instructing, by the processor, a performance of a physical move according to the instruction;
 receiving, by the processor, a movement sample by way of a first sensor of the device, wherein the movement sample is determined relative to a position of the set-top box, wherein the movement is determined according to a time difference of arrival at the device between two signals originating at the set-top box;
 evaluating, by the processor, the movement sample against a movement baseline for the person to determine a condition of the person; and
 transmitting, by the processor, the condition to the set-top box.

16. The method in claim 15, further comprising capturing, by the processor, a health sample from the person by way of a second sensor of the device, and
 wherein a first signal of the two signals originating at the set-top box comprises a data packet and a second signal of the two signals originating at the set-top box comprises an audio tone, wherein a distance between the device and the set-top box is determined according to a time difference of arrival between the first and second signals at the device.

17. The method in claim 16, wherein the health sample comprises one of a pulse, a blood oxygen level, a breathing pattern, a blood sugar level, or a blood pressure.

18. The method in claim 15, wherein the set-top box transmits the condition to an application server.

19. The method in claim 18, further comprising receiving, by the processor, a professional evaluation from a doctor in communication with the application server.

20. The method in claim 15, further comprising instructing, by the processor, the person to wear the device even outside a range of wireless communications with the set-top box.

* * * * *